United States Patent [19]

Iwasaki

[11] Patent Number: 4,807,963

[45] Date of Patent: Feb. 28, 1989

[54] LASER EMITTING DEVICE

[75] Inventor: Kenji Iwasaki, Utsunomiya, Japan

[73] Assignee: Kabushiki Kaisha Toshiba, Kawasaki, Japan

[21] Appl. No.: 124,416

[22] Filed: Nov. 18, 1987

Related U.S. Application Data

[63] Continuation of Ser. No. 865,480, May 21, 1986, abandoned.

[30] Foreign Application Priority Data

May 22, 1985 [JP] Japan ................... 60-109563

[51] Int. Cl.⁴ .................................. G02B 6/04
[52] U.S. Cl. .................. 350/96.24; 350/96.25; 350/96.1
[58] Field of Search ............... 350/96.1, 96.24–96.28, 350/96.16; 128/397, 398

[56] References Cited

U.S. PATENT DOCUMENTS 3,240,106  3/1966  Hicks, Jr. .................. 350/96.27 X
3,933,556  1/1976  Strack ...................... 350/96.25 X
4,653,495  3/1987  Nanaumi .................... 128/398 X

FOREIGN PATENT DOCUMENTS 0119108  9/1981  Japan ...................... 350/96.24
0019712  2/1982  Japan ...................... 350/96.24

OTHER PUBLICATIONS

Fisher et al; "Vibrating Display Unit"; *IBM Technical Disclosure Bulletin;* vol. 22, No. 1, Jun. 1979, pp. 6-8.

*Primary Examiner*—John D. Lee
*Assistant Examiner*—John Ngo
*Attorney, Agent, or Firm*—Finnegan, Henderson, Farabow, Garrett, & Dunner

[57] ABSTRACT

Silver light reflecting films are formed by depositing on the sides of on quartz glass prism-shaped light transmitters. A copper protective film is formed by depositing on the reflecting film. When laser beams are sequentially applied to the transmitters formed by bundling the transmitters, they repetitively propagate in the transmitters, while being repetitively mirror-reflected by the reflecting films. Since the laser beams are not reflected by total reflection as in the conventional device, an interval between the transmitters can be reduced. Therefore, it can prevent the beam from leaking in emitting the beam.

9 Claims, 2 Drawing Sheets

LASER EMITTING DEVICE

This application is a continuation of application Ser. No. 865,480, filed May 21, 1986, now abandoned.

BACKGROUND OF THE INVENTION

This invention relates to a scanning type laser emitting device used for treatment of a human nevus.

Human nevi such as birthmarks, moth patches, or freckles are formed by the storage of melanin pigments It is known that the incineration of melanin pigments by a ruby laser light and/or an argon laser light is effective for therapy of these nevi.

However, the laser light generally forms in its energy intensity a Gaussian distribution, and when the laser light produced from a laser generator is applied to the human skin, irregular incineration occurs on the skin, unpreferably reducing the treating effect.

A technique for uniformly forming the energy distribution by propagating the light while repetitively reflecting the light on the surfaces in light transmitting medium in the form of a transparent square bar (hereinafter abbreviated as the "light transmitter") made of acrylic material or optical glass is proposed as a technique for uniformly distributing the output energy of this laser light (Japanese Patent Laid-open No. 27816/1981). In this transmitter, the laser light is incident to the rod-shaped light transmitter and propagated in the transmitter while by a total reflection. Thus, the laser light emitted from the transmitter is uniformly distributed in the energy.

This technique is effective for therapy of the nevi, if a pulse laser light having large instantaneous output like a ruby laser light is used because of its large output density. However, the technique needs a long time to apply predetermined energy to the portion to be cured since the technique produces a small output density in case of using a laser light source capable of outputting only a continuous wave like an argon laser light. Thus, when the treatment is carried out by an argon laser light source, it is necessary to apply laser light for a long period. Therefore, heat is propagated to a range out of the region to be emitted, thereby thermally damaging the healthy tissue of the region not to be treated at the periphery of the nevus. Accordingly, it is not preferable, in view of the treating effect, to use the argon laser light so as to cure the nevus.

Another laser emitting device which produces a laser beam of high output density, though argon laser light, in a uniform energy density distribution is disclosed in Japanese Patent Application No. 203595/1982. In this device, as shown in FIG. 1, light transmitter bundle 2 in which nine prism-shaped light transmitters 4 are, for example, aligned in three rows in three columns is provided Laser beams are sequentially scanned and incident to the incident ends in respective transmitters 4. The laser beams are propagated while being fully reflected individually on the surfaces in the light transmitters, and emitted from the emitting ends after the energy density distribution becomes uniform. Since the section of bundle 2 has a size corresponding to the nevus portion to be cured, the sectional areas of respective transmitters 4 are small. Thus, the energy density (the emitting energy/the sectional area) of the laser beam can be sufficiently high.

In this case, the laser beam is transmitted while being totally reflected in the transmitter. The essential materials capable of transmitting the light and the refractive indexes are:

Quartz glass: 1.4602 (at 5461 Å)
Optical glass: 1.5187 (at 5461 Å)
Ethylene tetrafluoride: 1.35
Polypropylene: 1.49–1.50
Air: 1.00

When transmitter 4 is made of quartz glass or optical glass, ethylene tetrafluoride (Teflon: trade mark) or air which has a refractive index lower than that of transmitter 4 should be interposed at the sides (between the transmitters). In other words, the ethylene tetrafluoride is coated, a sheet of ethylene tetrafluoride is arranged on the sides of the transmitters, or air gaps are formed between the transmitters.

However, it is difficult to reduce the coating thickness of the ethylene tetrafluoride to 100 micron or less. Even if the sheet of the ethylene tetrafluoride is interposed between transmitters 4, it is also difficult to reduce the thickness of the sheet to 100 micron or less. Further, even if an air layer is interposed between the transmitters, it is also difficult to reduce the air gap to 100 micron or less. Thus, even if optical transmitter bundle 2 is constructed by bundling rod-shaped light transmitters 4, a light shielding layer having 100 micron or more is presented between the transmitters.

As a result, when a laser light is emitted to a portion to be treated by bundle 2, the portion corresponding to the light shielding layer between transmitters 4 of the portion to be emitted becomes a lattice shade to cause the portion to be emitted to apparently remain. In other words, the lattice-shaped unincinerated remainder occurs on the portion to be cured to be inconvenient in the treating effect.

SUMMARY OF THE INVENTION

It is an object of this invention to provide a laser emitting device which has a uniform energy distribution with high output density of a laser beam to extremely reduce the interval between light transmitters and capable of preventing a nevus portion from remaining unincinerated.

In order to achieve the above and other objects, there is provided according to the present invention a laser emitting device comprising:

a light transmitter bundle including a plurality of elongated light transmitters, each having a light incident terminal and a light emitting terminal at both longitudinal ends thereof, metallic reflecting films formed on the sides of the transmitters and constructed by arranging the light incident terminals and the light emitting terminals of the respective transmitters on the same surfaces, respectively, and bundling the transmitters, comprising:

a light source for irradiating a laser beam; and laser beam scanning means for scanning the light incident terminals with the laser beam by sequentially emitting the laser beam to the light incident terminals of a plurality of transmitters.

According to the invention, the laser beams incident to the respective transmitters are mirror-reflected by the metallic film, and propagated in the transmitter while being repetitively reflected. Thus, the energy density of the laser beam is formed uniformly. The plurality of transmitters are bundled to obtain a predetermining emitting area, and the sectional area of the transmitter is small Therefore, the laser beam of high energy density and high emitting area can be obtained.

Further, the feature of this invention resides in that the metallic film is disposed on the sides of the transmitter. In this invention, the laser beam is not fully reflected, but propagates while being repetitively mirror-reflected by the metallic film. Since the metallic film can be formed by depositing on the sides of the transmitter, the thickness of the metallic film can be reduced. Accordingly, the interval between the transmitters can be extremely shortened. Thus, since the interval between the transmitters is short, it can prevent the laser beam from leaking (remaining unincinerated) due to the presence of the interval. This is very effective in the treatment. Since the beam is not fully reflected, the incident angle of the beam to the incident terminal of the transmitter can be increased. Thus, the length of the transmitter can be shortened to readily manufacture the laser emitting device.

DETAILED DESCRIPTION OF THE PREFERRED EMBODIMENTS

Figure 1:
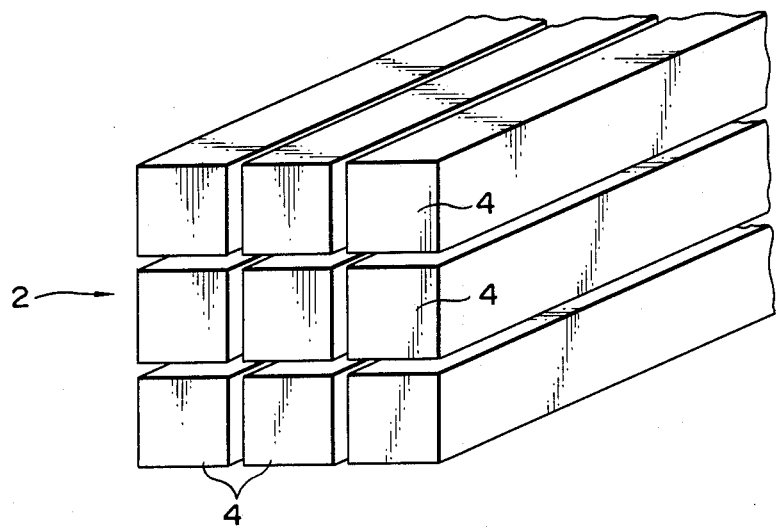
FIG. 1 is a perspective view showing a conventional light transmitter bundle.
Figure 3:
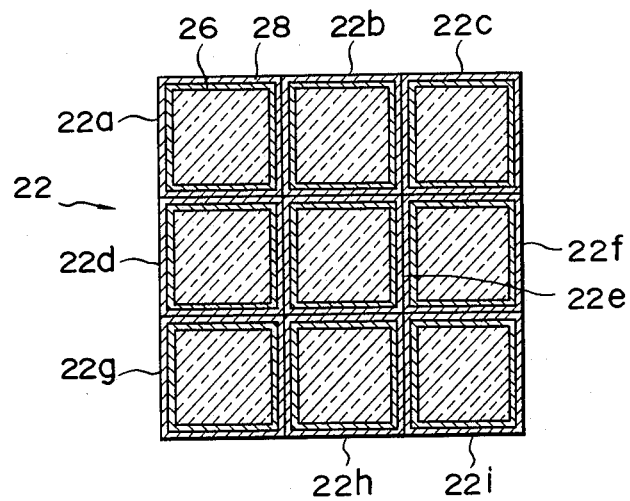
FIG. 3 is an enlarged sectional view of the light transmitter bundle of the device.
Figure 2:
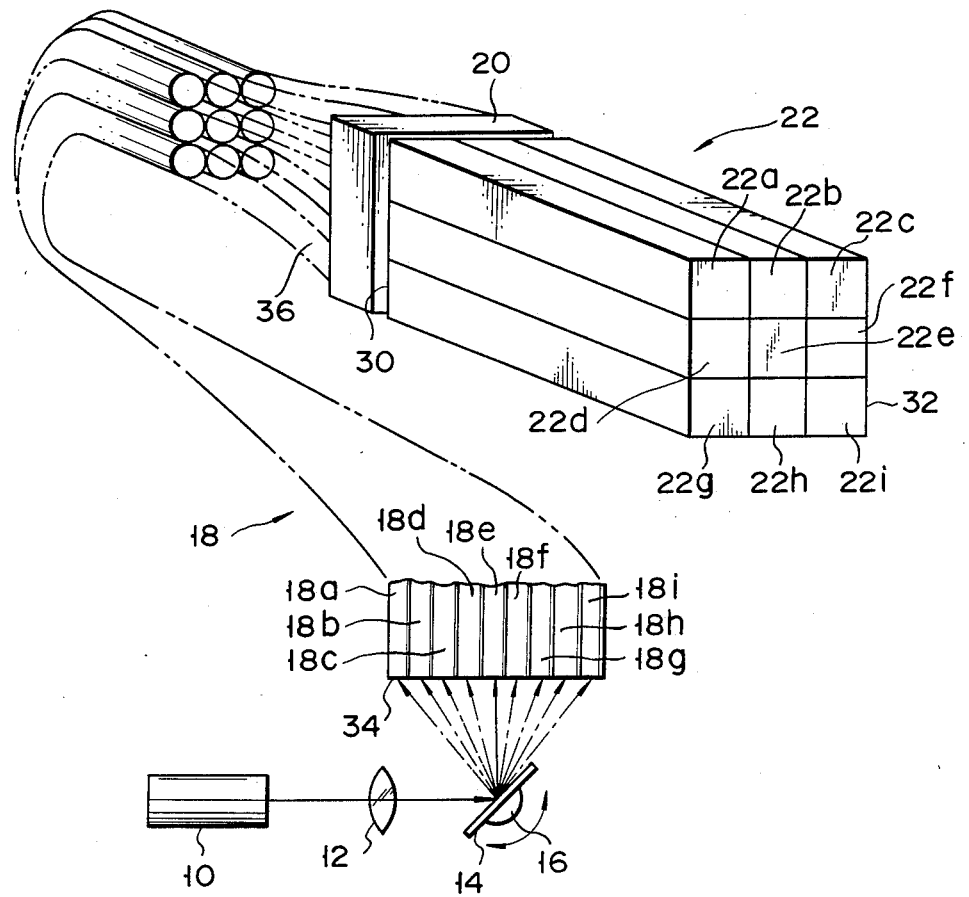
FIG. 2 is a view showing an embodiment of a laser beam emitting device according to the present invention.

FIG. 2 shows an embodiment of a laser beam emitting device according to the present invention. Condensing lens 12 and reflecting mirror 14 are arranged on the optical axis of laser generator 10. Mirror 14 is driven by drive member 16 such as a step motor so as to reciprocatingly rotate at the crossing point of the reflecting surface and the optical axis as a center. Laser beam from generator 10 is reflected by mirror 14, and achieves a scanning in a sector shape in a predetermined angle range from the central angle as designated by one-dotted chain line in FIG. 2. Light incident terminals 34 of bundle fibers 18 in which plurality (nine in the embodiment shown) of optical fibers 18a, 18b, 18c, 18d, 18e, 18f, 18g, 18h and 18i are bundled are arranged on the scanning line of the beam. Thus, the beam reflected by rotating mirror 14 scans the nine incident terminals of fibers 18 to be sequentially incident to the respective fibers. Emitting terminals 36 of fibers 18 are mounted in three rows and three columns in holder 20.

Optical transmitter bundle 22 is disposed oppositely to holder 20. Bundle 22 is constructed by aligning square prism-shaped light transmitters 22a, 22b, 22c, 22d, 22d, 22f, 22g, 22h and 22i in three rows and three columns in section. Transmitters 22a to 22i are formed of a light transmitting material such as glass, quartz or acryl, which has high light transmitter efficiency with respect to the light to be transmitted. These transmitters 22a to 22i are mirror-polished and finished. The longitudinal ends of transmitters 22a to 22i become light incident terminals 30 and light emitting terminals 32. Mirror-reflecting films 26 are, for example, formed by depositing silver on the sides of transmitters 22a to 22i. Since films 26 are formed by depositing, the thickness may be formed 1 to 2 micron. Copper is, for example, deposited on films 26 to prevent the silver from oxidizing to form protective film 28. Film 28 may be formed of any other material, such as nickel or chromium, which is hardly oxidized. Since film 28 can be formed by depositing, its thickness may be 1 to 2 micron. Therefore, an interval between adjacent transmitters 22a to 22i can be formed to 4 micron or less at the maximum in bundle 22. In other words, the width of the region which does not emit a light on the light emitting surface can be reduced to 4 microns or less, and the width is a sufficiently small value to prevent the nevus portion to be treated from remaining unincinerated. Therefore, the nevus portion to be treated can be continuously and uniformly emitted with the laser beam without substantially discontinuity.

Transmitters 22a to 22i are secured fixedly each other, with grease applied between them. Alternatively, transmitters 22a to 22i can be pressed to one another at end and are fixed to one another, or can be connected to one another with adhesive.

In the laser beam emitting device constructed as described above, the laser beam emitted from generator 10 is reflected by mirror 14, and incident to incident terminals 34 of fibers 18. Since mirror 14 reciprocatingly rotates by member 16, the beams scan light emitting terminals 34 of fibers 18a to 18i. Thus, the beams are sequentially incident to fibers 18a to 18i, and sequentially emitted from emitting terminals 36.

Since terminals 36 are held by holder 20 so as to correspond one by one to terminals 30 of bundle 22, the beams emitted from terminals 30 of fibers 18a to 18i are sequentially incident to terminals 30 of transmitters 22a to 22i. In other words, the beams scan terminals 20 of transmitters 22a to 22i, and sequentially incident into the transmitters. The beams are mirror-reflected by film 26 formed on the sides of transmitters 22a to 22i, and propagate in the transmitters. Thus, the energy distribution of the beams becomes uniform. Each transmitter has a small cross sectional area, e.g., 2 mm×2 mm. Nonetheless, when the transmitters are arranged in three rows and three columns, as uniform irradiation surface of 6 mm×6 mm will be provided. A principle of uniformly forming uniform laser light energy distribution by the optical transmitters is by mixing the beams by repeating the reflections a number of times. Thus, it is necessary to repeat the reflections of the beams at predetermined times or higher on the sides of the transmitters. When films 26 are formed on the sides of the transmitters as in this invention, the beams are propagated by mirror-reflections on films 26. However, if the ethylene tetrafluoride layer or air layer is interposed between the transmitters as in the conventional device, the beams are propagated by total-reflections on the sides of the transmitters. Thus, the incident angles of the beams to the transmitters are limited in the conventional device. However, in the mirror reflection as in this invention, no limit exists in the reflecting angles, and no restriction in the incident angles of the beams. Therefore, according to this invention to obtain the same number of reflections, the lengths of the transmitters can be reduced as compared with the conventional device. It is necessary to accurately mirror-polish the surface of the transmitters. Since the lengths of the transmitters are short as in this invention, the manufacture of the transmitters can be facilitated, and the mass productivity can be enhanced to reduce the fabricating cost.

A light loss exists in the reflection of films 26. The reflecting materials listed below exhibit the following reflectivities to light having a wavelength of 0.550 μm:

Silver: 97.9%
Gold: 81.7%
Copper: 66.9%

Aluminum 91.6%
Rhodium: 78.0%

Other reflecting materials can be used when light of a different wavelength is applied. Hence, the reflecting materials that can be used in the invention are not limited to those listed above.

Of the above materials, silver of the largest reflectivity has 2.1% of loss. On the other hand, a loss also exists when the laser beam is propagated in the transmitter. However, since the length of the transmitter can be shortened in the invention, the light loss in the transmitter is alleviated. Since the light loss in film 26 and the light loss in the transmitter at propagating time cancel to each other, the degree of the light loss in the comparison of the incident intensity of the transmitter with the emitting intensity does not become larger than that in the conventional device.

The present invention is not limited to the particular embodiments described above. Other changes and modifications can be made within the spirit and scope of the present invention. For example, laser beam scanning means is not limited to rotating mirror 14 and a plurality of optical fibers 18a to 18i shown in FIG. 2. The reflecting film is not limited to the case formed by depositing, but a metallic foil may be bonded to the sides of the transmitters. Further, the material for forming the reflecting film is not limited to the silver, but any material which has high reflectivity and high durability may be used. In addition, the number of the transmitters in the transmitter bundle is not limited to nine as in the above embodiment, but may be selected to sixteen or other numbers.

What is claimed is:

1. A laser emitting device for treatment of a human nevus comprising:

a light source for irradiating a laser beam;

a light transmitter bundle including a plurality of transparent prism-shaped transmitters for uniformly distributing an output energy of said light source onto a nevus, each of said transmitters having a light incident terminal and a light emitting terminal at respective longitudinal ends thereof and metallic reflecting films formed on the sides of said transmitters, and said light transmitter bundle constructed with said metallic reflecting films on adjacent sides of each transmitter being substantially contiguous and by arranging said light incident terminals and said light emitting terminals of the respective transmitters on the same surfaces, respectively; and laser beam scanning means for scanning said light incident terminals with a laser beam by sequentially emitting said laser beam to said light incident terminals of said transmitter.

2. A laser emitting device according to claim 1, wherein said transmitter is formed of one selected from the group consisting of quartz, optical glass and acryl.

3. A laser emitting device according to claim 1, wherein said reflecting film is formed of one selected from the group consisting of silver, gold, copper, aluminum and rhodium.

4. A laser emitting device according to claim 1, wherein protective films are formed on said metallic reflecting films.

5. A laser emitting device according to claim 4, wherein said protective films are formed of copper.

6. A laser emitting device according to claim 1, wherein said transmitters are secured fixedly each other, with grease between them.

7. A laser emitting device according to claim 1, wherein said laser beam scanning means comprises a reflecting mirror for reflecting a laser beam from a laser beam generator, a bundle fiber for leading the laser beam from the mirror to the transmitter, and a plurality of optical fibers respectively having light incident terminals and light emitting terminals, and drive means for driving the reflecting mirror to scan the light incident terminal of the optical fiber with the light reflected from the reflecting mirror.

8. A laser emitting device according to claim 7, wherein said laser beam scanning means has a holder for aligning the emitting terminal of the optical fiber to the light incident terminal of the transmitter.

9. A laser emitting device according to claim 1, wherein said metallic reflecting films on adjacent sides of each transmitter define the maximum distance between each of said adjacent transmitters.

* * * * *